United States Patent [19]

Mosimann

[11] 4,435,161

[45] Mar. 6, 1984

[54] DENTAL TURBINE

[76] Inventor: David Mosimann, Ch. des Grillons 13-15, CH-2504 Bienne 6, Switzerland

[21] Appl. No.: 395,084

[22] PCT Filed: Oct. 8, 1981

[86] PCT No.: PCT/CH81/00113

§ 371 Date: Jun. 10, 1982

§ 102(e) Date: Jun. 10, 1982

[87] PCT Pub. No.: WO82/01309

PCT Pub. Date: Apr. 29, 1982

[30] Foreign Application Priority Data

Oct. 10, 1980 [CH] Switzerland ................. 7576/80

[51] Int. Cl.³ ........................................... A61C 1/05
[52] U.S. Cl. ........................................... 433/132
[58] Field of Search ............... 433/117, 132, 126, 115, 433/133

[56] References Cited

U.S. PATENT DOCUMENTS 3,955,284  5/1976  Baison ................................. 433/132
4,225,308  9/1980  Lohn .................................. 433/132

*Primary Examiner*—Robert Peshock
*Attorney, Agent, or Firm*—McGlew and Tuttle

[57] ABSTRACT

In a dental turbine, having a laterally displaceably arranged rotor assembly including a shaft mounted in upper and lower ball bearings and having its lower end protruding through a bore provided in the nose of the turbine and forming a gap or space with the bore for accommodating the lateral displacement of the shaft lower end thereat a protective sleeve (1) is fitted to the outer ring (2) of the lower ball bearing, and extends below the bearing, then along the lower end of the shaft (4) and into the space (5) formed between the shaft (4) and the bore (6) in the nose (7) of the turbine to provide a relatively minute gap or space between the inner surface of the lower portion of the sleeve and the lower end of the shaft and a resultant reduced size gap or space between the outer surface of the lower portion of the sleeve and the inner surface of the bore in the nose.

The protective sleeve (1) which follows any lateral movement of the rotor assembly and a ring of soft material (13) received in compressed state between the outer surface of the lower portion of the sleeve and the inner surface (15) of the turbine head, i.e. rearwardly or upwardly of the bore in the nose, prevent waste material of any kind which might otherwise have penetrated into the interior of the turbine through the minute gap or space (10) and/or the reduced size gap or space (12), from reaching the vital parts of the rotor.

5 Claims, 2 Drawing Figures

DENTAL TURBINE

FIELD AND BACKGROUND OF THE INVENTION

A rotor of an air turbine for dental drills comprises a shaft mounted in ball bearings or in one or more air bearings. The shaft is provided with a chamber accommodating a mechanism for fixing the burr. The nose of the turbine, of course, is bored to receive a shaft passing therethrough.

In the head of the turbine, the rotor is suspended from rings of soft material or O-rings which thus support the turbine, particularly laterally. This means that the rotor may be displaced laterally upon a pressure exerted on the turbine head. In consequence, the diameter of the bore provided in the turbine nose must be much larger than that of the shaft, in order to prevent the rotating shaft from butting against and produce friction at the bore wall. A gap is therefore left between the shaft and the bore in the turbine nose through which dentine, powdered enamel, blood, filling residues, and other waste might infiltrate during the operation of the turbine. Such waste is projected up to the inside ball bearing, or the air bearing and the air inlets which thus become fouled and clogged. This strongly affects the reliability of dental turbines. Their ball bearings or air bearings and air inlets must periodically be cleaned or even replaced. Further, waste of any kind accumulating in the interior of the turbines may become a non-negligible source of infection.

SUMMARY OF THE INVENTION

The present invention is directed to a ball bearing or air cushion mounted dental turbine of such design that the various wastes which might penetrate therein in the way described in the foregoing is prevented from reaching the vital parts of the rotor, i.e. either the lower ball bearing or the air bearing and air inlets.

The inventive turbine is characterized by a protective sleeve which is fitted to the outer ring of the lower ball bearing or to the outside wall of the air bearing, and extends below the bearing and then along the shaft up to the gap between the shaft and the bore of the turbine nose. Further, a ring of soft material is received in compressed state between the outer surface of the lower portion of the protective sleeve and the inner surface of the turbine head.

DESCRIPTION OF THE PREFERRED EMBODIMENT

One embodiment of the invention is shown by way of example in the accompanying drawings.

Figure 1:
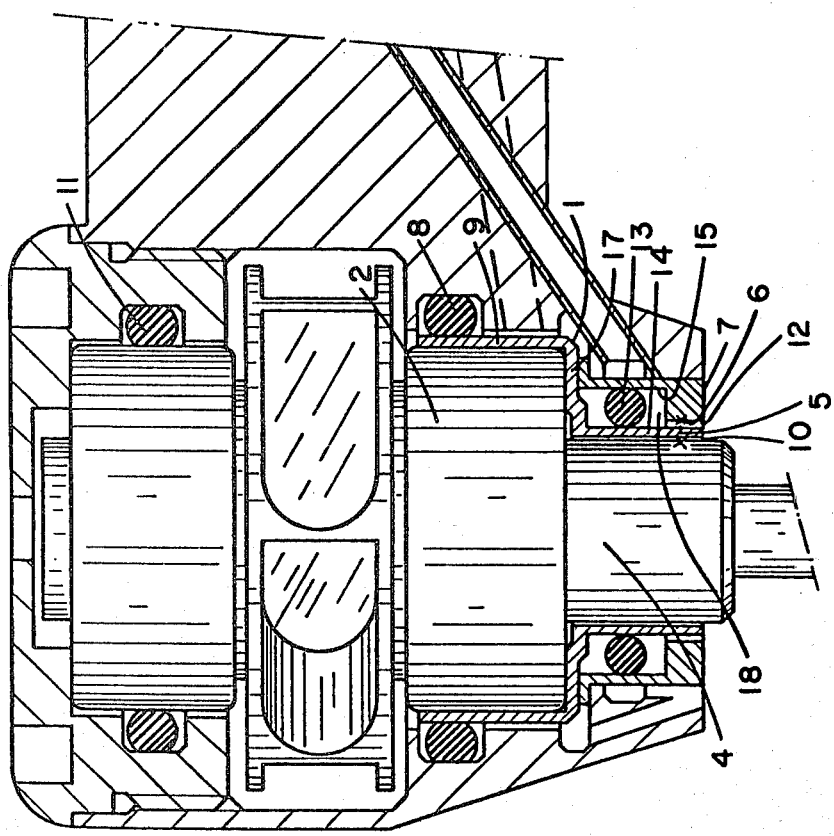
FIG. 1 is a sectional view of the turbine head.
Figure 2:
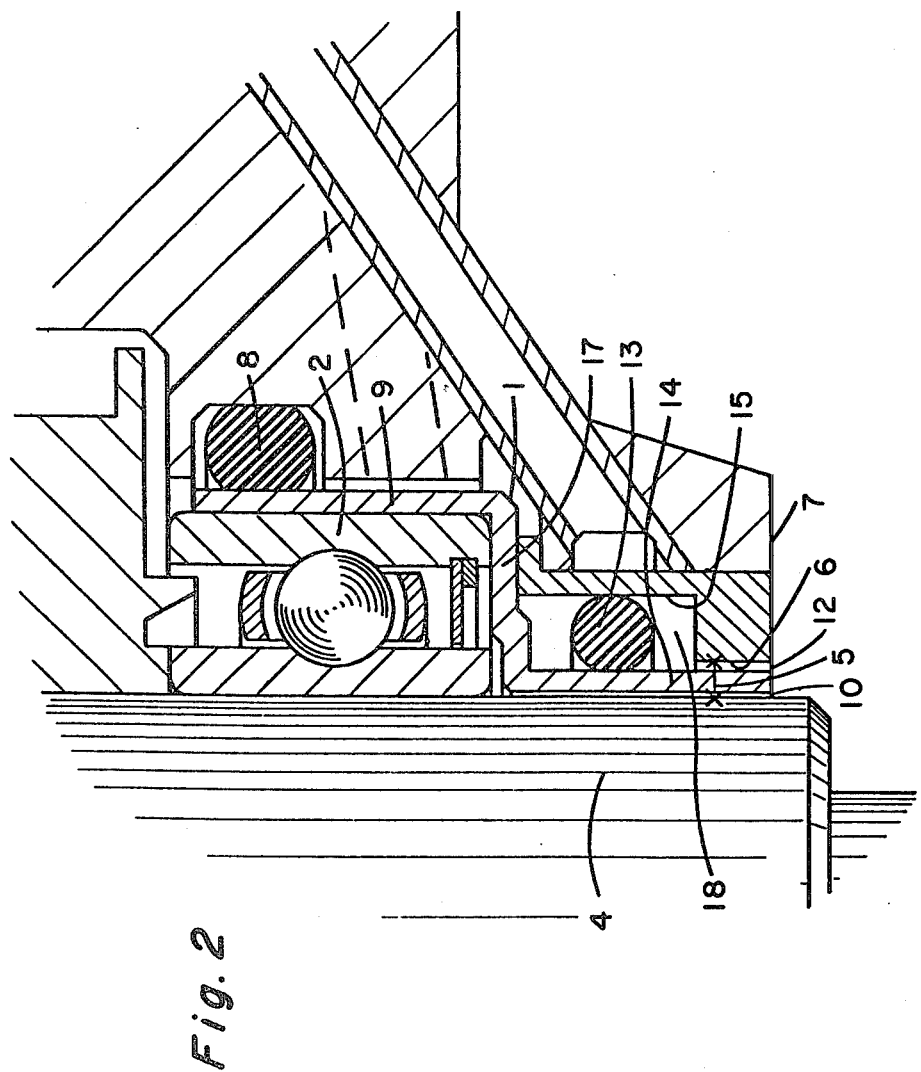
FIG. 2 is a partial sectional view of the protective sleeve mounted in place.

The protective sleeve 1 made in a single piece comprises an upper portion 9, an intermediate portion 17, and a lower portion 14. Upper portion 9 is fitted by its inner surface onto the outer ring 2 of the ball bearing. Protective sleeve 9 extends by its intermediate portion 17 below the ball bearing and, by its lower portion 14, along shaft 4 into space 5 formed between the shaft and the bore 6 provided in nose 7 of the turbine. The sleeve thus completely surrounds the outer ring 2 of the ball bearing, the bottom surface of this bearing, and the lower portion of shaft 4. The sleeve firmly fits the outer ring 2 of the ball bearing and, consequently, follows any lateral movement of the rotor assembly. The O-ring 8 providing suspension applies against the outer surface of the upper portion 9 of protective sleeve 1. A gap 10 must be provided between shaft 4 and the inner surface of lower portion 14 of protective sleeve 1, to avoid any friction between these elements during the rotation of shaft 4. A minute gap 10 may be provided, however, since protective sleeve 1 is firmly fitted to the rotor assembly.

Further, to insure that the rotor will remain virtually suspended from O-rings 8 and 11, a satisfactory gap 12 must be provided between the outer surface of lower portion 14 of protective sleeve 1 and bore 6 of nose 7 of the turbine.

With the turbine in operation, waste of any kind might penetrate therein, through gap 10 between shaft 4 and the inner surface of lower portion 14 of protective sleeve 1, or through gap 12 between the outer surface of lower portion 14 of protective sleeve 1 and bore 6 of nose 7 of the turbine.

However, gap 10 is very narrow and will hardly allow any waste particles to pass therethrough. Further, the rotary motion of shaft 4 tends to eliminate waste which might penetrate through gap 10.

Waste which might have penetrated through gap 12 into the interior of the turbine will accumulate in chamber 18 formed between inner surface 15 of the turbine head and the outer surface of lower portion 14 of protective sleeve 1, where the waste particles are retained by ring 13 of soft material received in compressed state in chamber 18.

I claim:

1. A dental turbine comprising a rotor assembly receiving turbine head forwardly terminating in a nose containing a turbine shaft accommodating bore which forms an inwardly facing bore surface, and a rotor assembly laterally displaceably received in the head and including a turbine shaft mounted for rotation in bearing means, such bearing means being positioned for lateral displacement relative to the head and including a correspondingly laterally displaceable bearing adjacent to the bore and having a rotatable inner bearing part connected to the shaft for movement therewith and a cooperating non-rotatable outer bearing part laterally displaceably positioned in the head, and such shaft having a forward portion forwardly of the bearing and extending through the bore in inwardly spaced relation to the bore surface and thereby defining a clearance space between the shaft and the bore surface for accommodating lateral displacement of the shaft relative to the head thereat, and a non-rotatable and correspondingly laterally displaceable protective sleeve fitted to the outer bearing part for lateral displacement therewith and extending therealong to the forward portion of the shaft and into the annular space and maintained in outwardly spaced relation to the forward portion of the shaft to permit unhindered rotation of the shaft and to provide a relatively minute clearance gap between the forward portion of the shaft and the adjacent portion of the sleeve in the clearance space for protecting against entry of external waste material thereat, and correspondingly maintained in inwardly spaced relation to the bore surface to provide a resultant reduced clearance space between the adjacent portion of the sleeve and the bore surface for similar protection against entry of such waste material thereat yet sufficient for accommodating lateral displacement of the forward portion of the shaft and the sleeve upon lateral displacement of the rotor assembly relative to the head.

2. Dental turbine according to claim 1, wherein compressible sealing means are selectively received operatively between the sleeve and the adjacent portion of the head for protection against further entry of any such waste material which may enter the reduced clearance space.

3. Dental turbine according to claim 1, wherein a ring of soft material is received in compressed state operatively between the sleeve and the adjacent portion of the head rearwardly of the bore for protection against further entry of any such waste material which may enter the reduced clearance space.

4. Dental turbine according to claim 1, wherein the bearing is a ball bearing having a rotatable inner bearing ring and a non-rotatable outer bearing ring, and the sleeve is fitted to the outer bearing ring and protectively encloses the adjacent portions of the bearing as well as the forward portion of the shaft.

5. Dental turbine according to claim 4, wherein a ring of soft material is received in compressed state operatively between the sleeve and the adjacent portion of the head rearwardly of the bore and forwardly of the ball bearing for protection against further entry of any such waste material which may enter the reduced clearance space.

* * * * *